United States Patent [19]

Felder et al.

[11] 4,321,118

[45] Mar. 23, 1982

[54] BIS BENZOYL SENSITIZERS FOR PHOTOPOLYMERIZATION OR PHOTO CROSS LINKING PROCESS AND COMPOSITION

[75] Inventors: Louis Felder, Basel; Rudolf Kirchmayr, Aesch; Rinaldo Hüsler, Basel, all of Switzerland

[73] Assignee: Ciba-Geigy Corporation, Ardsley, N.Y.

[21] Appl. No.: 105,744

[22] Filed: Dec. 19, 1979

Related U.S. Application Data

[63] Continuation-in-part of Ser. No. 970,016, Dec. 18, 1978.

[30] Foreign Application Priority Data

Dec. 22, 1977 [CH] Switzerland ............... 15884/77
Mar. 8, 1978 [CH] Switzerland ............... 2518/78
Sep. 18, 1978 [CH] Switzerland ............... 9723/78

[51] Int. Cl.³ ............................. C08F 2/50; C08J 3/28
[52] U.S. Cl. ......................... 204/159.18; 204/159.19; 204/159.20; 204/159.23; 204/159.24; 525/348; 525/375; 525/383; 526/204; 526/208; 430/281; 430/916; 430/919; 430/920; 430/921
[58] Field of Search ............... 204/159.23, 159.18, 204/159.20, 159.24, 159.19; 526/204, 208; 525/348, 375, 383

[56] References Cited

U.S. PATENT DOCUMENTS

| | | | |
|---|---|---|---|
| 3,974,053 | 8/1976 | Nemcek et al. | 204/159.23 |
| 3,988,228 | 10/1976 | Newland et al. | 204/159.23 |
| 4,040,923 | 8/1977 | Pacifici et al. | 204/159.23 |
| 4,101,584 | 7/1978 | Ranus et al. | 204/159.23 |
| 4,279,720 | 7/1981 | Berner | 204/159.16 |
| 4,284,485 | 8/1981 | Berner | 204/159.16 |

Primary Examiner—John C. Bleutge
Assistant Examiner—A. H. Koeckert
Attorney, Agent, or Firm—Wenderoth, Lind & Ponack

[57] ABSTRACT

Aromatic-aliphatic ketones of the formulae I, II, III or IV

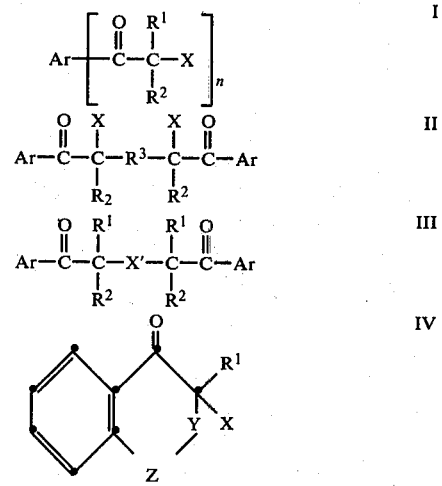

wherein n is 1 or 2, Ar is an aryl radical, $R^1$ and $R^2$ are monovalent aliphatic, cycloaliphatic or araliphatic radicals, $R^3$ is a direct bond or a divalent organic radical, X is a hydroxyl or amino group or the monovalent etherification or silylation products thereof, and X' is a divalent amino, ether or silyloxy group, Y is a direct bond or $CH_2$ and Z is O, S, $SO_2$, $CH_2$ or $C(CH_3)_2$, are suitable sensitizers for the photopolymerization of unsaturated compounds and for the photochemical crosslinking of polyolefins. Some of these compounds are novel and can be obtained by methods analogous to those for obtaining the known compounds of this type.

14 Claims, No Drawings

BIS BENZOYL SENSITIZERS FOR PHOTOPOLYMERIZATION OR PHOTO CROSS LINKING PROCESS AND COMPOSITION

This application is a continuation-in-part of application Ser. No. 970,016, filed Dec. 18, 1978.

The invention relates to the use of aromatic aliphatic ketones which are substituted in the α-position as sensitizers for the photopolymerisation of unsaturated compounds or for the photochemical crosslinking of polyolefins, as well as to the photopolymerisable and crosslinkable systems which contain such sensitizers.

Photochemical polymerisation processes have attained substantial importance in the art, especially in those cases where thin layers have to be hardened in a short time, for example in the hardening of varnish coatings or in the drying of printing inks. Compared with conventional hardening methods, UV irradiation in the presence of photosensitizers has a number of advantages, the most important of which is the great speed of photohardening. The speed is heavily dependent on the photosensitizer empolyed and there has been no lack of attempts to replace the conventional sensitizers by ever better and more effective compounds. Among the most effective photosensitizers are derivatives of benzoin, in particular the benzoin ethers described for example in German patent specification No. 1,694,149, derivatives of α-hydroxymethylbenzoin described in German Offenlegungsschrift No. 1,923,266, and the dialkoxyacetophenones and benzil monoketals described for example in German Offenlegungsschrift Nos. 2,261,383 or 2,232,365. α-Aminoacetophenones and α-diaminoacetophenones have recently been proposed as photosensitizers in U.S. Pat. No. 4,048,034 and α-hydroxy-α-alkylolacetophenones and their ethers in German Offenlegungsschrift No. 2,357,866. The shortcomings of these known photosensitizers are in some cases an insufficient storage life in the dark of the photopolymerisable systems mixed with such sensitizers. A number of benzoin derivatives tend to cause yellowing of the hardened compositions. Other sensitizers are insufficiently reactive—a feature which is observed in the relatively lengthy hardening times—or their solubility in the photopolymerisable systems is too low or they are rapidly rendered inactive by atmospheric oxygen. There is therefore a need in the art for photosensitizers which are readily soluble in the substrate and, while having a good storage life in the dark, initiate the photopolymerisation more rapidly and give a higher polymer yield per unit of time than the known photosensitizers. By using such improved photosensitizers it would be possible to exploit better the expensive industrial UV irradiation plants.

It has been found that compounds of the following formulae I, II, III and IV possess the required properties as photosensitizers. In particular, they effect a rapid photopolymerisation and do not have the shortcomings referred to or possess them to a much lesser degree than the known photosensitizers. Furthermore, they are suitable for the photochemical crosslinking of polyolefins.

The invention relates to the use of the compounds of the formulae I, II, III or IV

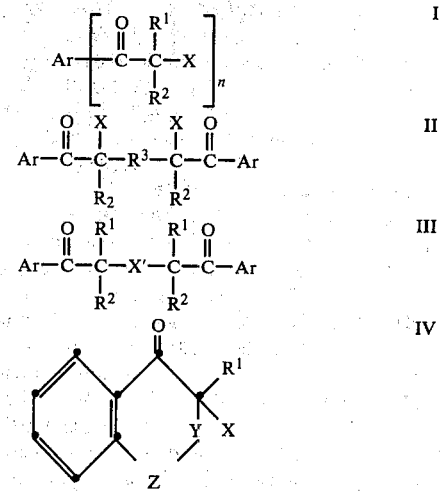

wherein n is 1 or 2, Ar if n is 1, represents $C_6$-$C_{14}$ aryl which is unsubstituted or substituted by one or more members selected from the group consisting of Cl, Br, CN, OH, $C_1$-$C_{12}$alkyl, —Oalk, —Ophenyl, —Salk, —$SCH_2CH_2OH$, Sphenyl, —$SO_2$alk, —$SO_2$phenyl, —COOalk, —$SO_2NH_2$, —$SO_2$NHalk, —$SO_2N(alk)_2$, —NHalk, —$N(alk)_2$, —NHCOalk or —NHCO-phenyl, or represents thienyl, pyridyl, furyl, indanyl or tetrahydronaphthyl, and alk represents a lower alkyl radical of 1 to 4 carbon atoms, and if n is 2, represents $C_6$-$C_{12}$ arylene, a -phenylene-T-phenylene group or a divalent 9,10-dihydroanthracene radical, X represents one of the groups —$NR^4R^5$, —$OR^6$, —$OSiR^7(R^8)_2$ or together with $R^1$ represents a —O—CH($R^9$)—, —O—CH($R^9$)—O—$(CH_2)_{1-2}$— or —O—$C_1$—$C_4$alkylene group, X' represents one of the groups —$NR^{10}$—, —$N(C_6$-$C_{14}aryl)$—,

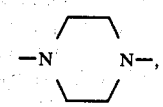

—$N(R^{10})$—$R^{11}$—$N(R^{10})$—, —O—, —O—$R^{12}$—O—, —O—$SiR^7R^8$—O— or —O—$SiR^7R^8$—O—$SiR^7R^8$—O—, Y represents a direct bond or —$CH_2$—, Z represents —O—, —S—, —$SO_2$—, —$CH_2$—, or —$C(CH_3)_2$—, T represents —O—, —S—, —$SO_2$—, —$CH_2$—, —$CH_2CH_2$—, —$CH_2OCH_2$—or —CH=CH—, $R^1$ in formula I, if n is 1 and X is —$OR^6$, represents $C_1$-$C_8$ alkyl which is unsubstituted or substituted by $C_2$-$C_8$acyloxy, —$NR^4R^5$, —COOalk or CN, or represents $C_3$-$C_5$alkenyl, $C_5$-$C_6$cycloalkyl or $C_7$-$C_9$-phenylalkyl, and in all other cases represents $C_1$-$C_8$alkyl which is unsubstituted or substituted by —OH, Oalk, $C_2$-$C_8$acyloxy, —$NR^4R^5$, —COOalk or —CN, or is $C_3$-$C_4$alkenyl, $C_5$-$C_6$cycloalkyl or $C_7$$C_9$phenylalkyl, $R^2$ has one of the meanings assigned to $R^1$ or represents a —$CH_2CH_2R^{13}$ group, or together with $R^1$ represents $C_2$-$C_8$alkylene or $C_3$-$C_9$oxa- or azaalkylene, $R^3$ represents a direct bond, $C_1$-$C_6$alkylene, $C_2$-$C_6$oxaalkylene, $C_2$-$C_6$thia-, S-oxathia- or S-dioxothiaalkylene, phenylene, diphenylene or a -phenylene-T-phenylene group, or together with both substituents $R^2$ and both carbon atoms to which these substituents are attached, forms a cyclopentane, cyclohexene, endomethylenecyclohexane or cyclohexane ring, $R^4$ represents $C_1$–$C_{12}$alkyl, $C_2$–$C_4$alkyl substituted by —OH, Oalk or —CN or represents $C_3$–$C_5$alkenyl, cyclohexyl, $C_7$–$C_9$phenylalkyl, phenyl or phenyl which is substituted by Cl, alk, OH, Oalk or —COOalk, $R^5$ represents $C_1$–$C_{12}$alkyl, $C_2$–$C_4$alkyl which is substituted by OH, Oalk or CN or represents $C_3$–$C_5$alkenyl, cyclohexyl or $C_7$–$C_9$phenylalkyl, or together with $R^4$ represents $C_4$–$C_5$alkylene which can be interrupted by —O— or —$NR^{14}$, or, in the case of compounds of the formula I, together with $R^2$ represents $C_1$–$C_9$alkylene or phenylalkylene or $C_2$–$C_3$oxa- or azaalkylene, $R^6$ represents hydrogen, $C_1$–$C_{12}$alkyl, $C_1$–$C_8$alkyl which is substituted by Cl, Br, OH, Oalk, Salk, $C_2$–$C_8$acyloxy, —COOalk, —CONHalk, —CON(alk)$_2$ or CN, or represents $C_3$–$C_5$alkenyl, cyclohexyl, benzyl, phenyl which is unsubstituted or substituted by Cl or alk, or 2-tetrahydropyranyl, $R_7$ and $R^8$ are the same or different and represent $C_1$–$C_4$alkyl or phenyl, $R^9$ represents hydrogen, $C_1$–$C_8$alkyl or $C_6$–$C_{14}$aryl, $R^{10}$ represents $C_1$–$C_8$alkyl, cyclohexyl or benzyl, $R^{11}$ represents $C_2$–$C_8$ alkylene, xylylene, phenylene or a -phenylene-T-phenylene group, $R^{12}$ represents $C_2$–$C_8$alkylene, $C_4$–$C_6$oxa- alkylene or xylylene, $R^{13}$ represents —$CONH_2$, —CONHalk, —CON(alk)$_2$, —P(O)(Oalk)$_2$, 2-pyridyl or 2-oxo-1-pyrrolidinyl, $R^{14}$ represents $C_1$–$C_4$alkyl, —$CH_2CH_2CN$ or —$CH_2CH_2COOalk$, as sensitizers for the photopolymerisation of unsaturated compounds and for the photochemical crosslinking of polyolefins.

These compounds are accordingly aromatic-aliphatic ketones, the α-carbon atom of which is tertiary and which are substituted by a hydroxyl or amino group or the etherification or silylation products thereof. The aliphatic residue can also be cycloaliphatic or araliphatic or linked to the aromatic residue with ring closure, which corresponds to the benzocyclic ketones of the formula IV.

Of the substituents listed above, $R^1$, $R^2$, $R^9$ and $R^{10}$ can be alkyl of 1 to 8 carbon atoms, for example methyl, ethyl, propyl, butyl, hexyl or octyl. $R^4$, $R^5$ and $R^6$ as alkyl can be unbranched or branched alkyl of 1 to 12 carbon atoms, for example methyl, ethyl, isopropyl, tert-butyl, isoamyl, n-hexyl, 2-ethylhexyl, n-decyl or n-dodecyl. Alk represents a lower alkyl radical of 1 to 4 carbon atoms, for example methyl, ethyl, isopropyl, n-butyl or tert-butyl.

$R^1$, $R^2$ and $R^6$ as hydroxyalkyl, alkoxyalkyl or acyloxyalkyl can be for example hydroxymethyl, 1-hydroxyethyl, 2-hydroxyethyl, 2-isopropoxyethyl, 1-hydroxyisobutyl, 1-acetyloxybutyl, 1-acryloyloxyhexyl, 1-hydroxyoctyl, 3-benzoyloxypropyl, methoxymethyl or isobutyloxymethyl. The acyl radical can be the radical of an aliphatic or aromatic carboxylic acid. Preferably they are 1-hydroxyalkyl radicals and their ethers or esters. $R^4$ and $R^5$ as hydroxyalkyl or alkoxyalkyl can be for example 2-hydroxyethyl, 2-butoxyethyl, 2-methoxypropyl, 3-hydroxypropyl or 2-ethoxybutyl. Preferably they are 2-hydroxyalkyl radicals and the ethers thereof.

$R^1$ and $R^2$ as alkyl which is substituted by —$NR^4R^5$ can be for example dibutylaminomethyl, 2-piperidinoethyl or 2-dimethylaminopropyl.

$R^1$, $R^2$, $R^4$, $R^5$ or $R^6$ as CN-substituted alkyl can be for example 2-cyanoethyl, 2-cyanopropyl or 4-cyanobutyl, whilst $R^1$, $R^2$ and $R^4$ can also be for example cyanomethyl, 2-cyanohexyl or 4-cyanooctyl. The 2-cyanoethyl radical is preferred.

$R^1$, $R^2$ and $R^6$ as alkyl substituted by —COOalk can be for example —$CH_2COOC_2H_5$, —$CH_2CH_2COOCH_3$, —$(CH_2)_3$—$COOCH_3$ or —$CH_2$—$CH(C_2H_5)$—$COOC_4H_9$. $R^6$ as alkyl substituted by —CONHalk or —CONH(alk)$_2$ can be for example —$CH_2CONHCH_3$, —$CH_2CH_2CON(CH_3)_2$ or —$CH_2CH(CH_3)$—$CONHC_4H_9$.

$R^1$, $R^2$, $R^4$, $R^5$ and $R^6$ as alkenyl can be for example allyl, methallyl or 2-butenyl.

$R^1$ and $R^2$ as cycloalkyl can be cyclopentyl or cyclohexyl. $R^1$, $R^2$, $R^4$ and $R^5$ as phenylalkyl can be for example benzyl, phenylethyl or dimethylbenzyl.

Ar as aryl or substituted phenyl can be for example phenyl, naphthyl, phenanthryl, anthracyl, diphenylyl, chlorophenyl, bromophenyl, dichlorophenyl, mesityl, isopropylphenyl, phenoxyphenyl, cyanophenyl, p-nonylphenyl, hydroxyphenyl, tolyl, tert-butylphenyl, xylyl, isopropylchlorophenyl, methoxyphenyl, ethoxyphenyl, phenoxyphenyl, chlorotolyl, bromoxylyl, methylthiophenyl, phenylthiophenyl, butylsulfophenyl, phenylsulfophenyl, ethoxycarbonylphenyl, tert-butoxycarbonylphenyl, methylaminosulfophenyl, dipropylaminosulfophenyl, dimethylaminophenyl, benzoylaminophenyl or acetylaminophenyl.

$R^9$ as aryl can be for example phenyl, tolyl, naphthyl, diphenylyl or phenanthryl.

$R^1$ and $R^2$ together can represent alkylene or oxaalkylene or azaalkylene. In this case, $R^1$ and $R^2$ together with the carbon atom to which they are attached form a cyclopropane, cyclobutane, cyclopentane, cyclohexane, cycloheptane, tetrahydrofurane, tetrahydropyrane, pyrrolidine or piperidine ring.

$R^2$ and $R^5$ together can represent alkylene or phenylalkylene of 1 to 9 carbon atoms or oxaalkylene or azaalkylene. In this case, $R^2$ and $R^5$ together with the carbon atom to which $R^2$ is attached and the nitrogen atom to which $R^5$ is attached form a 3- to 6-membered ring, for example an aziridine, azetidine, pyrrolidine, imidazolidine, piperidine, piperazine or morpholine ring.

$R^4$ and $R^5$ together can represent alkylene of 4 to 5 carbon atoms which can be interrupted by —O—or —$NR^{14}$—. In this case, $R^4$ and $R^5$ together with the nitrogen atom to which they are attached form a pyrrolidine, piperidine, morpholine, 4-alkylpiperazine, 4-cyanoethylpiperazine or 4-alkoxycarbonylethylpiperazine ring.

X and $R^1$ together can represent a —O—CH($R^9$)—, —O—CH($R^9$)—O—(CH$_2$)$_{1-2}$—or —0—$C_1$—$C_4$alkylene group. In this case, $R^1$ and X together with the carbon atom to which they are attached form an oxirane, oxetane, oxalane, tetrahydropyrane, 1,3-dioxolane or 1,3-dioxane ring which can be substituted by alkyl or aryl.

$R^3$ can be alkylene of 1 to 16 carbon atoms and $R^{11}$ and $R^{12}$ can be alkylene of 2 to 8 carbon atoms. Examples of such alkylene groups, within the stated number of carbon atoms, are: methylene, 1,2-ethylene, 1,3-propylene, 1,4-butylene, 2,2-dimethyl-1,3-propylene, 1,6-hexylene, 2-methyl-3-ethyl-1,4-butylene or 1,8-octylene. $R^3$ can also be oxaalkylene, thiaalkylene and mono- or dioxothiaalkylene of 2 to 6 carbon atoms, for example 2-oxa-1,3-propylene, 3-oxa-2,4-pentylene, 3-oxa-2,4-pentylene, 3-oxa-1,5-pentylene, —$CH_2SCH_2$—, —$CH_2CH_2SOCH_2CH_2$— or —$(CH_2)_3$-$SO_2$—$(CH_2)_3$—.

Ar can be arylene of 6 to 12 carbon atoms, for example phenylene, naphthylene or diphenylene.

If Y is a direct bond, the compounds of the formula IV constitute derivatives of indanone, cumarone or thiocumaranone. If Y is CH₂, they are derivatives of tetralone, chromanone or thiochromanone.

A particular object of the invention is the use of compounds of the formula I or II, wherein X is a —NR⁴R⁵ group. These compounds are arylalkyl ketones which are branched at the α-carbon atom and substituted by amino groups.

A further particular object of the invention is the use of compounds of the formula I or II, wherein X represents a —OR⁶ group. These compounds are arylalkyl ketones which are branched in the α-position and substituted by hydroxyl or ether groups.

Yet a further object of the invention is the use of compounds of the formula I or II, wherein X represents a —OSiR⁷(R⁸)₂ group. These compounds are arylalkyl ketones which are branched in the α-position and substituted by siloxy groups. The —OSiR⁷(R⁸)₂ group is for example trimethylsiloxy, dimethylphenylsiloxy, methyldiphenylsiloxy or triphenylsiloxy.

Preferably, the invention is concerned with the use of compounds of the formulae I, II, III or IV, wherein n is 1 or 2, Ar, if n is 1, represents $C_6$–$C_{14}$aryl which is unsubstituted or substituted by one or more members selected from the group consisting of Cl, Br, $C_1$–$C_{12}$alkyl, —Oalk, —Ophenyl, —COOalk, —N(alk)₂ or —NHCOalk, or represents indanyl, or tetrahydronaphthyl, and alk represents a lower alkyl radical of 1 to 4 carbon atoms, and, if n is 2, represents $C_6$–$C_{12}$arylene or a -phenylene-T-phenylene group, X represents one of the groups —NR⁴R⁵ or —OR⁶, X' represents one of the groups

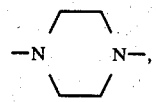

—N(R¹⁰)—R¹¹—N(R¹⁰)— or —O—R¹²—O, Y represents a direct bond or —CH₂—, Z represents —O—, —CH₂ or —C(CH₃)₂—, T represents —O—, —CH₂— or —CH₂CH₂—, R¹ in formula I, if n is 1 and X is —OR⁶, represents $C_1$–$C_8$alkyl which is unsubstituted or substituted by —COOalk or CN, or represents $C_7$–$C_9$-phenylalkyl, and in all other cases represents $C_1$–$C_8$ alkyl which is unsubstituted or substituted by —OH, Oalk, —COOalk or —CN, or is $C_7$–$C_9$phenylalkyl, R² has one of the meanings assigned to R¹ or is $C_3$–$C_4$alkenyl or a —CH₂CH₂R¹³ group, or together with R¹ represents $C_2$–$C_6$alkylene or $C_3$–$C_4$oxa- or azaalkylene, R³ represents a direct bond or $C_1$–$C_6$alkylene or together with both substituents R² and both carbon atoms to which these substituents are attached forms a cyclopentane or cyclohexane ring, R⁴ represents $C_1$–$C_{12}$alkyl, $C_2$–$C_4$alkyl which is substituted by OH, Oalk or CN or represents $C_3$–$C_5$alkenyl, R⁵ represents $C_1$–$C_{12}$alkyl, $C_2$–$C_4$alkyl which is substituted by OH, Oalk or CN or represents $C_3$–$C_5$ alkenyl, or together with R⁴ represents $C_4$–$C_5$alkylene which can be interrupted by —O— or —NR¹⁴, R⁶ represents hydrogen, $C_1$–$C_{12}$alkyl, $C_1$–$C_6$alkyl which is substituted by Cl, Br, OH, Oalk, —COOalk or CN, or is $C_3$–$C_5$ alkenyl, benzyl, phenyl, or together with R² represents $C_3$–$C_4$alkylene or —CH₂—O—CH₂—, R¹⁰ represents $C_1$–$C_8$alkyl, R¹¹ represents $C_2$–$C_8$ alkylene, R¹² represents $C_2$–$C_8$alkylene, $C_4$–$C_6$oxaalkylene or xylylene, R¹³ represents —CONH₂, —CONH—alk, —CON(alk)₂, —P(O)(Oalk)₂ or 2-pyridyl, and R¹⁴ represents $C_1$–$C_4$alkyl, —CH₂CH₂CN or —CH₂CH₂—COOalk.

Among these compounds, preferred compounds are those of the formula I, especially those compounds of the formula I in which n is 1 and X is OH and R¹ and R² together represent $C_2$–$C_5$alkylene.

Most preferably, the invention is concerned with the use of compounds of the formulae I, II or III, wherein n is 1 or 2, Ar, if n is 1, represents $C_6$–$C_{14}$aryl which is unsubstituted or substituted by halogen, $C_1$–$C_{12}$alkyl or Oalk, or represents indanyl or tetrahydronaphthyl, and alk represents a lower alkyl radical of 1 to 4 carbon atoms, and, if n is 2, represents $C_6$–$C_{12}$arylene or a -phenylene-T-phenylene group, X represents one of the groups —NR⁴R⁵ or —OR⁶, X' represents one of the groups

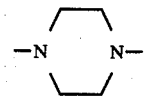

or —O—R¹²—O—, T represents —O—, —CH₂— or —CH₂CH₂—, R¹ represents $C_1$–$C_8$-alkyl, R² represents $C_1$–$C_8$alkyl or $C_3$–$C_4$alkenyl, R³ represents a direct bond or $C_1$–$C_6$alkylene, R⁴ represents $C_1$–$C_{12}$alkyl, R⁵ represents $C_1$–$C_{12}$alkyl or together with R⁴ represents $C_4$–$C_5$alkylene which can be interrupted by —O— or —NR¹⁴—, R⁶ represents hydrogen, $C_1$–$C_{12}$alkyl, $C_1$–$C_6$alkyl which is substituted by OH, Oalk, COOalk or CN, or represents $C_3$–$C_5$alkenyl, benzyl, phenyl, or together with R² represents —CH₂—O—CH₂—, R¹² represents $C_2$–$C_8$alkylene and R¹⁴ represents $C_1$–$C_4$alkyl.

Among these compounds, those compounds of the formula I or II are preferred in which X represents allyloxy, $C_1$–$C_6$hydroxyalkoxy or alkoxyalkoxy, —OCH₂CH₂CN, —OCH₂CH₂COOalk, benzyloxy or phenyloxy, or together with R² represents —O—CH₂—O—, and also the compounds of the formulae I, II or III in which Ar represents p-phenoxyphenyl or a tetrahydronaphthalene radical.

Examples of eligible compounds of the formula I, wherein n is 1, are: 2-hydroxy-2-methyl-propiophenone, 2-hydroxy-2-ethyl-propiophenone, 2-hydroxy-2-butyl-propiophenone, 2-methoxy-2-methyl-propiophenone, 2-hydroxy-2-methyl-(p-chloropropiophenone), 2-hydroxy-2-methyl-(3,4-dichloropropiophenone), 2-hydroxy-2-methyl-(p-methoxypropiophenone), 2-hydroxy-2-methyl-(2,4-dimethoxypropiophenone), 2-hydroxy-2-methyl-(p-phenoxypropiophenone), 2-hydroxy-2-methyl-(p-acetylaminopropiophenone), 2-hydroxy-2-methyl-(p-methylpropiophenone), 2-methoxy-2-methyl-(o-methylpropiophenone), 2-hydroxy-2-methyl-(m-methylpropiophenone), 2-hydroxy-2-methyl-(2,4-dimethylpropiophenone), 2-hydroxy-2-methyl-(3,4-dimethylpropiophenone), 2-hydroxy-2-methyl-(p-butylpropiophenone), 2-hydroxy-2-methyl-(p-tert.-butylpropiophenone), 2-hydroxy-2-methyl-(p-isopropylpropiophenone), 2-hydroxy-2-methyl-(p-octylpropiophenone), 2-hydroxy-2-methyl-(p-laurylpropiophenone), 2-methoxy-2-methyl-(o-chloropropiophenone), 2-methoxy-2-methyl-(o-methyl-propiophenone), 2-hydroxy-2-methyl-(p-methylthio-propiophenone), 2-hydroxy-2-methyl-(p-dimethylaminopropiophenone), 2-hydroxy-2-methyl-(p-carboethoxy-propiophenone), 2-phenoxy-2-methylpropiophenone 2-allyloxy-2-methyl-propiophenone, 2-benzyloxy-2-methylpropiophenone, 2-(2-methoxycarbonylethoxy)-2-methyl-propiophenone, 2-(2-cyanoethoxy)-2-methyl-propiophenone, 2-ethoxy-2-methyl-propiophenone, 2-methoxyethoxy-2-methyl-propiophenone, 2-hydroxymethoxy-2-methylpropiophenone, 2-hydroxyethoxy-2-methylpropiophenone, 2-acetoxymethoxy-2-methylpropiophenone, 2-benzoyloxymethoxy-2-methylpropiophenone, 2-(o-hydroxyphenoxy)-2-methylpropiophenone, 3-benzoyl-3-hydroxyheptane, 2-benzoyl-2-hydroxypentane, 3-benzoyl-3-hydroxypentane, 2-(2-carboethoxyphenoxy)-2-methylpropiophenone, 2-methyl-2-piperidino-2-phenyl-3-hydroxypropiophenone, 2-methyl-2-morpholino-3-phenyl-3-hydroxypropiophenone, 2-methyl-2-dimethylamino-3-phenyl-3-hydroxy-propiophenone, α-hydroxy-α-α-bis-(cyanoethyl)-acetophenone, γ-hydroxy-γ-benzoylpimelate diethylether, 2-hydroxy-2-methyl-3-phenyl-3-dimethylaminopropiophenone, 2-di-(2-hydroxyethyl)-amino-2-methyl-3-phenylpropiophenone, 2-methyl-2,3-dipiperidino-3-phenylpropiophenone, 2,3-bis-(dimethylamino)-3-phenylpropiophenone, 2-hydroxy-2,3-dimethyl-3-phenyl-3-dimethylamino-propiophenone, 2-dimethylamino-2-methylpropiophenone, 2-diethylamino-2-methylpropiophenone, 2-dibutylamino-2-methylpropiophenone, 2-di-hydroxyethylamino-2-methylpropiophenone, 2-piperidino-2-methylpropiophenone, 2-(2-methylpiperidino)-2-methylpropiophenone, 2-morpholino-2-methylpropiophenone, 2-piperazino-2-methylpropiophenone, 2-(4-methyl-piperazino)-2-methylpropiophenone, 2-(4-carboethoxyethylpiperazino)-2-methyl-propiophenone, 2-pyrrolidino-2-methylpropiophenone, 2-methylphenylamino-2-methylpropiophenone, 1-benzoylcyclohexanol, 1-benzoyl-cyclohexanol, 1-benzoyl-cyclopentanol, 1benzoyl-cyclopropanol, 3-p-methoxybenzoyl-3-dimethylaminoheptane, 6-(2-hydroxyisobutyryl)-tetraline, 5-(2-hydroxyisobutyryl)-indane, 6-(2-dimethylamino-isobutyryl)-tetraline, 6-(2-morpholino-isobutyryl)-tetraline, 6-(2-piperidino-isobutyryl)-tetraline, 6-(2-piperazino-isobutyryl)-tetraline, 2-(2-methoxybenzoyl)-2-diallylaminopropane, 2-(2-thenoyl)-2-piperidinopropane, 2-(2-naphthoyl)-2-acetoxybutane, 2-p-phenylbenzoyl-2-di-(2-hydroxyethyl)-aminopropane, 1-methyl-2-o-chlorobenzoyl-piperidin, 1-benzyl-2-benzoyl-3-phenylaziridine, 1-cyclohexyl-2-benzoyl-3-phenylaziridine, 2-o-toluyl-2-(trimethylsiloxy)-propane, 2-hydroxy-2-methyl(p-isopropylpropiophenone), 2-hydroxymethoxy-2-methylpropiophenone, 2-hydroxymethoxy-2-methyl-(2,5-dimethylpropiophenone), 2-hydroxymethoxy-2-methyl-(p-isopropylpropiophenone), 5-methyl-5-benzoyl-1,3-dioxolane, 2,5-dimethyl-5-benzoyl-1,3-dioxolane, 2-phenyl-5-methyl-5-benzoyl-1,3-dioxolane, 5-methyl-5-(p-isopropylbenzoyl)-1,3-dioxolane, 2,3-epoxy-2-methyl-3-phenylpropiophenone, 2-acetoxymethoxy-2-methylpropiophenone, 2-benzoyloxymethoxy-2-methylpropiophenone, 2-hydroxy-2-methyl-3-dimethylaminopropiophenone, 2-methoxy-2-methyl-3-dimethylaminopropiophenone, 2-hydroxy-2-methyl-3-morpholinopropiophenone, 2-hydroxy-2-methyl-4-N,N-diethylcarbamoylbutyrophenone, 2-morpholino-2-methyl-4-N,N-diethylcarbamoylbutyrophenone, 2-hydroxy-2-methyl-4-(2-pyridyl)-butyrophenone, 2-hydroxy-2-methyl-4-diethylphosphonobutyrophenone, 2-hydroxy-2-benzyl-propiophenone, 2-hydroxy-2-(p-methylbenzyl)-propiophenone, 2-hydroxy-2-cyclohexylpropiophenone, 2-hydroxy-2-cyclopentylpropiophenone, 2-(2-hydroxyethoxy)-2-methylpropiophenone, 2-hydroxy-2-allylpropiophenone, 2-hydroxy-2-methyl-4-(2-oxo-1-pyrrolidinyl)-butyrophenone, 2-methylthio-2-methylpropiophenone.

Examples of compounds of the formula I, wherein n is 2, are: 4,4'-bis-(α-hydroxy-isobutyryl)-diphenyl oxide, 4,4'-bis-(α-hydroxy-isobutyryl)-diphenyl, 4,4'-bis-(α-hydroxy-isobutyryl)-diphenyl sulfide, 4,4'-bis-(α-hydroxy-isobutyryl)diphenyl methane, 4,4'-bis-(α-piperidino-isobutyryl)-diphenyl oxide, 4,4'-bis-[α-(isopropylamino)-isobutyryl]-diphenyl, 4,4'-bis-(α-benzoyloxy-isobutyryl)-diphenyl oxide, 4,4'-bis-(α-hydroxy-isobutyryl)-diphenyl ethane.

Examples of compounds of the formula II are: 1,4-diphenyl-2,3-dimethyl-2,3-dihydroxy-butanedione-1,4, 2,4-dibenzoyl-2,4-dihydroxypentane, 2,9-dibenzoyl-2,9-dimethyl-3,8-dioxadecane, 2,7-dibenzoyl-2,7-dimethyl-3,6-dioxaoctane, 1,6-diphenyl-2,5-dimethyl-2,5-dihydroxy-hexanedione-1,6, 1,4-diphenyl-2,3-dimethyl-2,3-bis-(dimethylamino)butanedione-1,4, 1,4-diphenyl-2,3-dimethyl-2,3-dipiperidylbutanedione-1,4, 1,2-bis-hydroxy-1,2-bis-benzoyl-cyclohexane, 1,2-bis-dimethylamino-1,2-bis-benzoyl-cyclohexane, 1,2-bismorpholino-1,2-bis-benzoyl-cyclohexane, bis-(3-hydroxy-3-benzoylbutyl)-sulfone.

Examples of compounds of the formula III are: 1,4-bis-(1-benzoyl-isopropyl)-piperazine, 2,7-dibenzoyl-2,7-dimethyl-3,6-dioxaoctane, 2,9-dibenzoyl-2,9-dimethyl-3,8-dioxadecane, 2,6-dibenzoyl-2,6-dimethyl-3,5-dioxaheptane, N,N-bis-(α-benzoyl-isopropyl)-butylamine, N,N'-dimethyl-N,N'-bis-(α-benzoyl-isopropyl)-ethylenediamine.

Examples of compounds of the formula IV are: 1-oxo-2-dimethylamino-2-methyl-1,2,3,4-tetrahydronaphthalene, 1-oxo-2-hydroxy-2-methyl-1,2,3,4-tetrahydronaphthalene, 1-oxo-2-hydroxy-2-methylindane.

Some of the compounds of the formulae I, II, III and IV are known compounds, and others are novel.

Known compounds are those of the formula I, wherein n is 1, Ar represents phenyl, phenyl which is substituted by methyl or methoxy, or is furyl, $R^1$ and $R^2$ are methyl or $R^1$ and $R^2$ together represent alkylene and X is hydroxyl, methoxy or nitrophenoxy.

Known compounds are those of the formula I, wherein n is 1, Ar represents phenyl, chlorophenyl or diphenylyl, $R^1$ and $R^2$ are methyl or morpholinomethyl, or $R^1$ and $R^2$ together are alkylene and X is a —$NR^5R^6$ group, in which each of $R^5$ and $R^6$ is alkyl or benzyl or $R^5$ and $R^6$ together represents alkylene or oxaalkylene.

A known compound is also a compound of the formula II, wherein Ar represents phenyl, $R^1$ represents methyl, X represents hydroxy and $R^3$ is a direct bond.

The known compounds have up to now not been proposed as photosensitizers.

The compounds of the formulae I, II, III or IV, in so far as they are novel, also constitute an object of the invention. Accordingly, the invention also relates to:

(a) Compounds of the formula I, wherein n is 1, Ar represents $C_{10}C_{14}$aryl, $C_6$–$C_{14}$aryl which is substituted by one or more members selected from the group consisting of CN, OH, —Ophenyl, —Salk, —$SO_2$alk, —$SO_2$phenyl, —COOalk, —$SO_2NH_2$, —$SO_2$NHalk, —$SO_2$N(alk)$_2$, —NHalk or —NHCOalk or represents thienyl, pyridyl, indanyl or tetrahydronaphthyl, X is OH or —Oalk, and $R^1$ and $R^2$ are as previously defined.

(b) Compounds of the formula I, wherein n is 1, X is a —$OR^6$ group and $R^6$ represents $C_1$–$C_6$alkyl which is substituted by OH or Oalk or represents allyl, cyclohexyl, benzyl, phenyl which is unsubstituted or substituted by Cl or alk, or together with R² represents C₃-C₄alkylene or —CH₂—O—CH₂—, and Ar, R¹ and R² are as previously defined.

(c) Compounds of the formula I, wherein n is 1, X is —OSiR⁷(R⁸)₂ or together with R¹ represents one of the groups —O—CH(R⁹)—, —O—CH(R⁹)—O—(CH₂)₁₋₂— or —OC₁—C₄alkylene, R⁷ is C₂-C₄ alkyl or phenyl, and Ar, R¹, R² and R⁸ are as previously defined.

(d) Compounds of the formula I, wherein n is 1, Ar is phenyl, halogenphenyl or diphenylyl, X is a —NR⁴R⁵ group, R¹ is C₂-C₈alkyl, C₁-C₈alkyl which is substituted by OH, Oalk, C₂-C₈acyloxy, —COOalk or CN, or is C₅-C₆cycloalkyl or C₇-C₉phenylalkyl, R² has one of the meanings assigned to R¹ or is Allyl or a —CH₂CH₂R¹³ group or together with R¹ is C₄-C₆alkylene or C₃-C₄oxa- or azaalkylene, and R⁴, R⁵ and R¹³ are as previously defined.

(e) Compounds of the formula I, wherein n is 1, Ar is phenyl which is substituted by CN, OH, alk, Oalk, —Ophenyl, —Salk, —SO₂alk, —SO₂phenyl, —COOalk, —SO₂NH₂, —SO₂NHalk, —SO₂N(alk)₂, NHalk, —N(alk)₂ or —NHCOalk or is naphthyl, thienyl, pyridyl, furyl, indanyl or tetrahydronaphthyl, X is a —NR⁴R⁵ group and R¹, R², R⁴ and R⁵ are as previously defined.

(f) Compounds of the formula I, wherein n is 2 and Ar, X, R¹ and R² are as previously defined.

(g) Compounds of the formula II, wherein R³ is a direct bond, X is one of the groups —NR⁴R⁵, —OR⁶, OSiR⁷(R⁸)₂, R⁶ is C₁-C₁₂alkyl, C₂-C₄alkyl which is substituted by OH or Oalk or is allyl, cyclohexyl, benzyl, phenyl which is unsubstitued or substituted by Cl or alk, and Ar, R², R⁴, R⁵, R⁷ and R⁸ are as previously defined.

(h) Compounds of the formula II, wherein R³ represents C₁-C₆ alkylene, C₂-C₆oxaalkylene, C₂-C₆thia-, S-oxothia- or S-dioxothiaalkylene, phenylene, diphenylene or a -phenylene-T-phenylene group, and Ar, R², X and T are as previously defined.

(i) Compounds of the formula III, wherein Ar, R¹, R² and X' are as previously defined.

(k) Compounds of the formula IV, wherein R¹, X, Y and Z are as previously defined.

These novel compounds can be prepared by methods analogous to those for obtaining the known compounds, whereby different methods are possible.

Accordingly, the compounds of the formula I can be prepared from aromatic-aliphatic ketones by the following reaction steps:

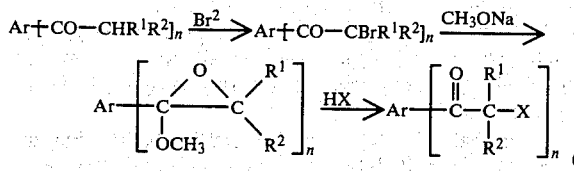

As HX it is possible to use amines [C. L. Stevens, Ch. Hung Chang, J. Org. Chem. 27 (1962), 4392] or water or carboxylic acids [C. L. Stevens, E. Farkas, J. Am. Chem. Soc. 74 (1952), 618 and C. L. Stevens, S. J. Dykstra, J. Am. Chem. Soc. 75 (1953), 5976].

In many cases the direct reaction of the α-bromoketones to give compounds of the formula I

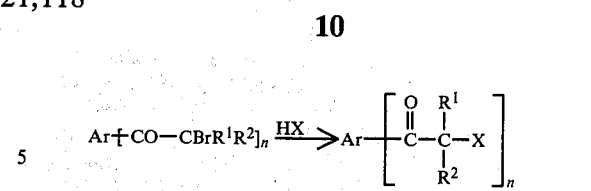

is also possible, for example with amines, alkali hydroxides or alkali phenoxides. Instead of bromine compounds it is also possible to use the corresponding chlorine compounds.

The resulting hydroxyketones of the formula I (X=OH) can be etherified or O-silylated by the conventional methods.

Compounds of the formula III are obtained by using a difunctional compound of the formula H—X'—H instead of the monofunctional compound HX in the above reactions.

The compounds of the formula II can be prepared analogously to those of the formula I by using diketones of the general formula

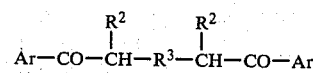

The compounds of the formula IV are obtained in analogous manner starting from cyclic ketones of the formula

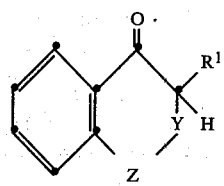

Compounds of the formula I, wherein R¹ is a substituted alkyl group, can be obtained from the compounds of the formula Ar—[CO—CH(R²)—X]ₙ by reaction with aldehydes (R¹=hydroxyalkyl) or with a vinyl compound which is capable of addition, for example with acrylates or acrylonitrile. In the same way, a —CH₂CH₂—R¹³ group can be introduced as R², starting from a compound Ar—[CO—CH(R¹)—X]ₙ. If both R¹ and R² are substituted alkyl, then both substituents can be introduced jointly by reaction of a compound Ar—[CO—CH₂—X]ₙ with at least 2 moles of an aldehyde or a vinyl compound. The corresponding alkoxyalkyl and acyloxyalkyl groups can be obtained from the hydroxyalkyl groups R¹ and/or R² by etherification or esterification. Compounds of the formulae II, III and IV containing substituted alkyl groups as R¹ or R² can be obtained in analogous manner.

Compounds in which X together with R¹ is a —O—CH (R⁹) group are α-oxydoketones and can be obtained by epoxidation of the corresponding α-vinyl ketones. Reaction of the oxydoketones with secondary amines affords compounds in which either X is OH and R¹ is an aminoalkyl group, or in which X is NR⁴R⁵ and R¹ is a hydroxyalkyl group.

Addition of bromine to the α-vinyl ketones yields α,β-dibromoketones of the formula Ar—[CO—CBr(R¹)—CBralk]ₙ.

Reaction of the dibromoketones with one mole of a primary amine yields the corresponding α-aziridinoketones [J. Am. Chem. Soc. 65 (1943), 312], and reaction with 2 moles of a secondary amine yields compounds of the formula I, wherein X is —NR⁴R⁵ and R² is an aminoalkyl radical [J. Am. Chem. Soc. 74 (1952), 1886].

Aminoalkyl groups $R^1$ and/or $R^2$ can also be introduced by the Mannich reaction, wherein ketones for the formula Ar—[CO—CHR¹—X]ₙ or Ar—[CO—CH₂—X]ₙ are reacted with 1 or 2 moles of formaldehyde and a secondary amine.

Whereas all these methods of synthesis start from an aromatic-aliphatic ketone into which a substituent X is introduced in a different manner, it is also possible in specific cases to introduce the substituent X during the ketone synthesis by the Friedel-Crafts reaction in accordance with the reaction scheme:

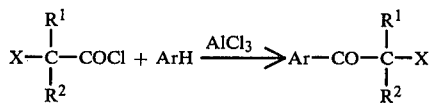

This presupposes that the substituent X is not attacked under the conditions of the Friedel-Crafts reaction. In this way it is possible for example by using heterocyclic carboxylic acid chlorides to prepare compounds of the formula I, in which X and $R^1$ together with the carbon atom to which they are attached form a heteroring.

According to the invention, the compounds of the formulae I, II, III and IV can be used as sensitizers for the photopolymerisation of unsaturated compounds or systems which contain such compounds.

Such compounds are for example unsaturated monomers, such as esters of acrylic or methacrylic acid, for example methylacrylate, ethylacrylate, n- or tert-butylacrylate, isooctylacrylate or hydroxyethylacrylate, methyl or ethylmethacrylate, ethylene diacrylate, neopentyl diacrylate, trimethylolpropane trisacrylate, pentaerythritol tetraacrylate or pentaerythritol trisacrylate; acrylonitrile, methacrylonitrile, acrylamide, methacrylamide, N-substituted acrylamides and methacrylamides; vinyl esters, such as vinyl acetate, vinyl propionate, vinyl acrylate or vinyl succinate; other vinyl compounds, such as vinyl ethers, styrene, alkyl styrenes, halostyrenes, divinyl benzene, vinyl naphthalene, N-vinylpyrrolidone, vinyl chloride or vinylidene chloride; allyl compounds, such as diallyl phthalate, diallyl maleate, triallyl isocyanurate, triallyl phosphate or ethylene glycol diallyl ether and the mixtures of such unsaturated monomers.

Photopolymerisable compounds are in addition unsaturated oligomers or polymers and the mixtures thereof with unsaturated monomers. These include thermoplastic resins which contain unsaturated groups, such as fumaric acid ester groups, allyl groups or acrylate or methacrylate groups. These unsaturated groups are usually bound through functional groups to the main chain of these linear polymers. Mixtures of oligomers with simply and poly-unsaturated monomers are very important. Examples of such oligomers are unsaturated polyesters, unsaturated acrylic resins and isocyanate or epoxide modified acrylate oligomers as well as polyether acrylate oligomers. Examples of poly-unsaturated compounds are in particular the acrylates of diols and polyols, for example hexamethylene diacrylate or pentaerythritol tetracrylate. Acrylates are also preferred as simply unsaturated monomers, for example butyl acrylate, phenyl acrylate, benzyl acrylate, 2-ethylhexyl acrylate or 2-hydroxypropyl acrylate. By choosing from the different representatives of the three components, the opportunity is afforded to vary the consistency of the unpolymerised mixture as well as the plasticity of the polymerised resin.

In addition to these three-component mixtures, two-component mixtures especially are of great importance among the polyester resins. These usually consist of an unsaturated polyester and a vinyl compound. The unsaturated polyesters are oligomer esterification products of at least one unsaturated dicarboxylic acid, for example maleic, fumaric or citraconic acid, and usually of at least one saturated dicarboxylic acid, for example phthalic acid, succinic acid, sebacic acid or isophthalic acid, with glycols, for example ethylene glycol, propanediol-1,2, di- or triethylene glycol or tetramethylene glycol, whilst monocarboxylic acids and monoalcohols are generally also used concurrently for the modification. These unsaturated polyesters are normally dissolved in a vinyl or allyl compound, styrene being preferably used for this purpose.

Photopolymerisable systems which are used for the different purposes usually contain, in addition to the photopolymerisable compounds and the photosensitizer, a number of other ingredients. It is therefore often customary to add heat inhibitors in order to prevent a premature polymerisation, especially during the preparation of the systems by mixing the components. Hydroquinone, hydroquinone derivatives, p-methoxyphenyl, β-naphthylamine or β-naphthols are used for example for this purpose. Furthermore, small amounts of UV absorbers can be added, for example those of the benztriazole or benzophenone type.

To increase the storage life in the dark, it is possible to add copper compounds, such as copper naphthenate, copper stearate or copper octoate, phosphorus compounds, such as triphenylphosphine, tributylphosphine, triethyl phosphite, triphenyl phosphite or tribenzyl phosphate, quaternary ammonium compounds, such as tetramethylammonium chloride or, trimethylbenzylammonium chloride, or hydroxylamine derivatives, for example N-diethylhydroxylamine. In addition, the photopolymerisable systems can contain chain transfer agents, for example N-methyl-diethanolamine, triethanolamine or cyclohexene.

In order to exclude the inhibiting action of atmospheric oxygen, paraffin or similar wax-like substances are frequently added to photohardening systems. On account of their poor solubility in the polymer, these substances float at the beginning of the polymerisation and form a transparent surface layer which prevents the entry of air. The atmospheric oxygen can also be deactivated by introducing autoxidisable groups, for example allyl groups, into the resin to be hardened.

Depending on the end-use, photopolymerisable systems also contain fillers, such as silicic acid, talc or gypsum, pigments, dyes, fibres, thixotropic agents or levelling agents.

Combinations with known photosensitizers, such as benzoin ethers, dialkoxy acetophenones or benzyl ketals, can also be used. Combinations of the photosensitizers of the invention with amines and/or aromatic ketones can be used especially for the photopolymerisation of thin layers and printing inks. Examples of amines are triethylamine, N-methyldiethanolamine, N-dimethylethanolamine or p-dimethylaminobenzoate. Examples of ketones are benzophenone, substituted benzophenone derivatives, Michler's ketone, anthraquinone and anthraquinone derivatives, as well as thioxanthone and the derivatives thereof.

Photohardening is of great importance for printing inks, since the drying time of the binder is a decisive factor in the production speed of printing products and should be in the order of fractions of seconds. The sensitizers of the invention are also very suitable for photohardening systems for the manufacture of printing plates. Mixtures of soluble linear polyamides with photopolymerisable monomers, for example acrylamides, and a photosensitizer, are usually employed for this purpose. Films or plates prepared from these systems are exposed via the negative (or positive) of the original and the unhardened portions are subsequently eluted with a solvent.

A further field of use of UV hardening is metal coating, for example in the varnish coating of metal sheeting for tubes, cans or bottle caps, as well as the UV hardening of plastic coatings, for example of floor or wall coverings based on PVC.

Exemplary of the UV hardening of paper coatings is the colourless varnish coating of labels, gramophone record sleeves or book jackets.

According to the invention, the compounds of the formulae I, II, III and IV can also be used as sensitizers for the photochemical crosslinking of polyolefins, for example polypropylene, polybutene, polyisobutylene and also copolymers, for example ethylene/propylene copolymers, but preferably polyethylene of low, medium or high density.

The photosensitizers are advantageously used for the above fields of use in amounts of 0.1 to 20% by weight, preferably about 0.5 to 5% by weight, based on the photopolymerisable or crosslinkable system. The term "system" is to be understood as meaning the mixture of the photopolymerisable or crosslinkable compound, the photosensitizer and the other fillers and additives, as it is used in the respective application.

The addition of the photosensitizers to the photopolymerisable systems is accomplished in general by simple stirring, since most of these systems are fluid or readily soluble. Usually the sensitizers of the invention dissolve in the system, thereby ensuring their uniform distribution and the transparency of the polymers.

The polymerisation is carried out by the known methods of polymerisation by irradiation with light which is rich in shortwave radiation. Suitable light sources are for example mercury medium pressure, high pressure and low pressure lamps, as well as superactinic fluorescent tubes, the emission peaks of which are in the range between 250 and 400 nm.

The following Examples describe the manufacture and use of compounds of the formula I in more detail. Parts and percentages are by weight.

MANUFACTURE AND PROPERTIES OF THE COMPOUNDS USED IN EXAMPLES 1 TO 6

The compounds listed in Table 1 were obtained by one or more of the methods A to L.

Method A: Chlorination of aromatic-aliphatic ketones

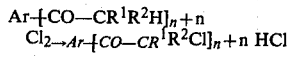

The ketone is dissolved in an inert solvent, preferably in tetrachloromethane, and the calculated amount of chlorine is introduced into the solution at 40°–80° C. Nitrogen is then introduced to remove dissolved HCl. Finally, the solvent is distilled off. Purification of the chloroketone is usually not necessary and the product can subsequently be reacted by method D, F or H.

Method B: Bromination of aromatic-aliphatic ketones

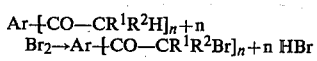

The calculated amount of bromine is added dropwise at room temperature to a solution of the ketone, for example in CCl₄. Working up and further processing are effected as in Method A.

Method C: Chlorination with sulfuryl chloride

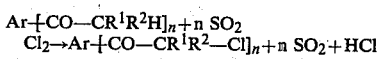

The sulfuryl chloride is added dropwise at 40° C. to a solution of the ketone in CCl₄. Working up and further processing as in Method A.

Method D: Preparation of the epoxide intermediate

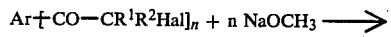

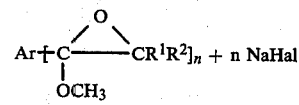

Hal = Cl or Br

The haloketone is dissolved in methanol and a solution of the stoichiometric amount of sodium methoxide in methanol is added dropwise at reflux temperature. The methanol is then distilled off and the residue is poured into ice-water and extracted with ether. The ethereal solution is washed with water, dried over Na₂SO₄, dried and concentrated. The residue is purified by recrystallisation or vacuum distillation. The epoxide can subsequently be reacted by Method E or G.

Method E: Hydrolysis of the epoxide

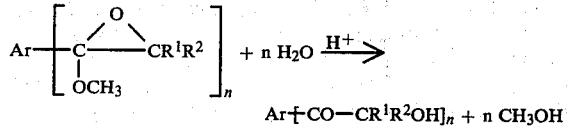

The epoxide is covered with 2 to 5 times its weight of water and the mixture is refluxed for 1 to 2 hours with the addition of a catalytic amount of mineral acid. After cooling, the reaction mixture is extracted with ether. The ethereal solution is washed with water, dried over Na₂SO₄, and concentrated. The residue (crude hydroxyketone) is purified by distillation or crystallisation or column chromatography. The properties of the pure α-hydroxyketones are indicated in Table 1.

Method F: α-Hydroxyketones from α-haloketones

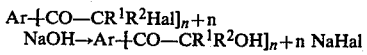

The α-haloketone is refluxed in dilute or concentrated sodium hydroxide solution (20% excess of NaOH). When the hydrolysis is complete (check by chromatography), the crude hydroxyketone is isolated and purified as described in Method E. The pure hydroxyketones are listed in Table 1.

Method G: α-Aminoketones from the epoxides

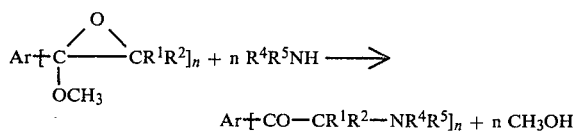

The epoxide is treated with the stoichiometric amount of the amine, either without a solvent or with the addition of a small amount of toluene or xylene, and reacted for about 10 to 20 hours at 100°-200° C. When using low boiling amines, for example dimethylamine or diethylamine, the reaction is carried out in an autoclave. The reaction mixture is diluted with benzene and extracted with dilute hydrochloric acid. The aqueous acid solution is made alkaline with NaOH and extracted with ether. The ethereal solution is washed with water, dried over $Na_2SO_4$ and concentrated. The crude product is purified by distillation or crystallisation. The α-amineketones are listed in Table 1.

Method H: α-Aminoketones from the α-haloketones $$Ar+CO-CR^1R^2Hal]_n+2n \, R^4R^5NH \rightarrow Ar+CO-CR^1R^2-NR^4R^5]_n+n \, R^4R^5NH_2Hal$$

The α-haloketone, undiluted or diluted with toluene, is mixed with 2 molar equivalents of the amine and the mixture is heated for 10 to 20 hours to 100°-200° C. When using low boiling amines, for example dimethylamine or diethylamine, the reaction is carried out in an autoclave. Isolation and purification are effected as in Method G.

Method I: Introduction of a carbalkoxyethyl group

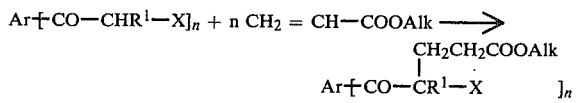

The ketone is dissolved in dimethyl sulfoxide. To the solution are then added 1.1 molar equivalents of NaOH in the form of 4 N sodium hydroxide solution and, with cooling, 1.1 molar equivalents of acrylate are added dropwise at room temperature. The reaction mixture is diluted with ice-water and extracted with toluene. The toluene solution is washed neutral with water, dried over $Na_2SO_4$ and concentrated. The crude product is purified by column chromatography or crystallisation.

Method K: Etherification of hydroxyketones $$Ar+CO-CR^1R^2-OH]_n+n \, R^6Hal+n \, NaOH \rightarrow Ar+CO-CR^1R^2-OR^6]_n+n \, NaHal$$

The α-hydroxyketone is dissolved in about 4 times its weight of dimethyl sulfoxide and, while cooling to 10°-20° C. and with stirring, 1 molar equivalent of the alkyl halide $R^6Hal$ and 1 molar equivalent of concentrated sodium hydroxide solution are added dropwise simultaneously from two drip funnels. The reaction mixture is then stirred for 3 hours at room temperature. Precipitated sodium halide is then removed by filtration, the filtrate is washed with water, dried over $Na_2SO_4$ and concentrated. The crude product is purified by column chromatography, crystallisation or vacuum distillation. Examples of eligible halogen compounds are methyl iodide, isopropyl bromide, allyl bromide, cyclohexyl bromide, benzyl chloride or ethyl chloroacetate. Instead of using an alkyl halide, it is also possible to use a dialkyl sulfate or alkylaryl sulfonate as etherifying reagent.

Method L: Cyclisation of X and $R^1$

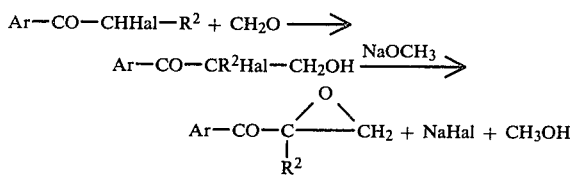

Paraformaldehyde is dissolved in 20 times its weight of methanol. To the solution is then added 1 molar equivalent of sodium methoxide (dissolved in a small amount of methanol). While cooling to 0°-5° C., a concentrated solution of the α-haloketone is added dropwise. The reaction mixture is subsequently stirred for 1 hour at 5°-10° C. and for 1 hour at room temperature. The reaction mixture is diluted with ether to 2 to 3 times its volume and poured into ice-water. The aqueous mixture is extracted 3 times with ether and the ethereal extracts are washed with water, dried over $Na_2SO_4$ and concentrated. The crude product is purified by distillation or column chromatography.

TABLE 1

| Compound | Formula | Method of manufacture | Purification | Physical properties (°C.) |
|---|---|---|---|---|
| 1 | ![structure] | B + D + G | dist. | b.p.$_{0.2}$ 61° |
| 2 | ![structure] | A + D + G | cryst. (petr. ether) | b.p.$_{0.02}$ 110–112° m.p. 78–80° C. |
| 3 | ![structure] | A + D + E or B + F | dist. | b.p. 120° |
| 4 | ![structure] | B + D + E | cryst. (petr. ether) | m.p. 42–50° |

TABLE 1-continued

| Compound | Formula | Method of manufacture | Purification | Physical properties (°C.) |
|---|---|---|---|---|
| 5 | (phenyl)-C(O)-C(OH)(cyclic) | B + D + E | chromat. | oil |
| 6 | (thienyl)-C(O)-C(CH₃)₂-OH | B + D + E | dist. | b.p.₁₀ 150°* |
| 7 | H₃C-(phenyl)-C(O)-C(CH₃)₂-OH | B + D + E | dist. | b.p.₀.₁ 150°* |
| 8 | H₃C-(dimethylphenyl)-C(O)-C(CH₃)₂-OH | B + D + E | dist. | b.p.₀.₁ 140°* |
| 9 | H₃C-(dimethylphenyl)-C(O)-C(CH₃)₂-OH | B + D + E | dist. | b.p.₀.₁ 130°* |
| 10 | (2,6-dimethylphenyl)-C(O)-C(CH₃)₂-OH | B + D + E | dist. | b.p.₀.₁ 130°* |
| 11 | H₃C-O-(phenyl)-C(O)-C(CH₃)₂-OH | B + D + E | dist. | b.p.₀.₁ 150°* |
| 12 | H₃C-O-, O-CH₃, Br-(phenyl)-CO-C(CH₃)₂-OH | B + D + E | cryst. (diethyl ether) | m.p. 92–96° |
| 13 | (H₃C)₂CH-(phenyl)-C(O)-C(CH₃)₂-OH | B + D + E | dist. | b.p.₀.₀₁ 74° |
| 14 | H₃C-O-, O-CH₃, Cl-(phenyl)-CO-C(CH₃)₂-OH | C + F | chromat. | m.p. 103–105° |
| 15 | (naphthyl)-C(O)-C(CH₃)₂-OH | C + F | dist. | m.p. 54–58° b.p.₀.₁ 165° |
| 16 | Cl-(phenyl)-C(O)-C(CH₃)₂-OH | B + D + E | dist. | b.p.₀.₁ 150°* |
| 17 | (phenyl)-O-(phenyl)-C(O)-C(CH₃)₂-OH | C + D + E | dist. | b.p.₀.₀₅ 180°* |
| 18 | H₃C-S-(phenyl)-C(O)-C(CH₃)₂-OH | B + D + E | dist. | wax b.p.₀.₁ 150°* |
| 19 | (naphthyl)-CO-C(CH₃)₂-OH | B + D + E | dist. | b.p.₀.₂ 140°* α: β-isomer 6:1 |

TABLE 1-continued

| Compound | Formula | Method of manufacture | Purification | Physical properties (°C.) |
|---|---|---|---|---|
| 20 | Ph-S-C6H4-C(O)-C(CH3)2-OH | B + D + E | dist. | b.p.$_{0.1}$ 180°* |
| 21 | HO-C(CH3)2-C(O)-C6H4-O-C6H4-C(O)-C(CH3)2-OH | B + D + E | dist. | b.p.$_{0.05}$ 220°* wax |
| 22 | Ph-C(O)-C(C2H5)(C4H9)-OH | B + F | dist. | b.p.$_{0.1}$ 150°* |
| 23 | HO-C(CH3)2-C(O)-C6H4-S-C6H4-C(O)-C(CH3)2-OH | B + D + E | cryst. (diethyl ether) | m.p. 90–91° |
| 24 | Ph-C(O)-C(CH3)2-N(C2H5)2 | B + D + G | dist. | b.p.$_{0.1}$ 150°* |
| 25 | Ph-C(O)-CH[N(CH3)2]- (cyclohexyl) | B + D + G | chromat. | oil |
| 26 | Ph-C(O)-C(CH3)2-N(piperazine)N-C(CH3)2-C(O)-Ph | B + D + G | cryst. (ethanol) | m.p. 141–143° |
| 27 | Ph-C(O)-C(CH3)2-N(piperazine)N-H | B + D + G | dist. | b.p.$_{0.1}$ 150°* |
| 28 | (thienyl)-C(O)-C(CH3)2-N(morpholine) | B + D + G | dist. | b.p.$_{0.1}$ 150°* |
| 29 | 3,4-(CH3)2-C6H3-C(O)-C(CH3)2-N(morpholine) | B + D + G | cryst. (diisopropyl ether) | m.p. 110–112° |
| 30 | Ph-C(O)-C(CH3)2-N(piperidine) | C + H or A + D + G | dist. | m.p. 34°* 0.05 150° |
| 31 | 4-Cl-C6H4-C(O)-C(CH3)2-N(piperidine) | B + H | dist. | b.p.$_{0.1}$ 150°* |
| 32 | 4-CH3-C6H4-C(O)-C(CH3)2-N(piperidine) | B + D + G | dist. | b.p.$_{0.1}$ 150°* |
| 33 | 4-CH3O-C6H4-C(O)-C(CH3)2-N(piperidine) | B + H | dist. | bp.$_{0.2}$ 180°* |
| 34 | Ph-O-C6H4-C(O)-C(CH3)2-N(piperidine) | C + H | dist. | b.p.$_{0.1}$ 200°* |
| 35 | 4-CH3S-C6H4-C(O)-C(CH3)2-N(morpholine) | B + D + G | dist. | m.p. 68–71° b.p.$_{0.1}$ 210°* |
| 36 | 2-(1-hydroxy-1-methylethyl)indan-1-one | F | chromat. | m.p. 54° |

TABLE 1-continued

| Compound | Formula | Method of manufacture | Purification | Physical properties (°C.) |
|---|---|---|---|---|
| 37 | Ph-C(=O)-C(CH3)(N(CH3)2)-CH2CH2COOCH3 | J | chromat. | oil |
| 38 | Ph-C(=O)-C(CH3)(OH)-CH2CH2COOCH3 | J | chromat. | oil |
| 39 | Ph-C(=O)-C(CH3)2-OCH3 | K | chromat. | oil |
| 40 | Ph-C(=O)-C(CH3)2-OCH2CH=CH2 | K | chromat. | oil |
| 41 | Ph-C(=O)-C(CH3)2-N(piperazine)N-CH3 | B + D + G | | m.p. 38–41° |
| 42 | Ph-C(=O)-C(CH3)(epoxide) | C + L | dist. | b.p.$_{24}$ 130° |

*temperature of the air bath in bulb tube destillation.

EXAMPLE 1

A resin mixture consisting of 80 parts of Plex 6616 (acrylate resin, available from Röhm, Darmstadt), 20 parts of trimethylolpropane-trisacrylate and 2 parts of photosensitizer is applied with a film drawing device to glass plates in a thickness of 40μ. These films are exposed to air for about 20 seconds and then irradiated with a mercury medium pressure lamp (Hanovia device, Model 45080). In the course of the irradiation, the samples are passed underneath the lamp on a conveyer belt at a speed such that the effective exposure time is 0.16 second per run.

Table 2 indicates the number of runs (R) which were necessary in order to obtain non-tacky films. In addition, the hardness of the film was determined with a pendulum device by the method of König. The final column indicates the storage stability of the resin-photosensitizer mixture in the dark at 60° C.

TABLE 2

| Photosensitizer | Runs | Pendulum hardness according to König after number of runs (R) | | | Storage stability in days |
|---|---|---|---|---|---|
| 1 | 4 | 78(4R) | 94(6R) | 98(8R) | >30 |
| 2 | 4 | 101(4R) | 114(4R) | 116(8R) | >30 |
| 3 | 4 | 116(4R) | 119(8R) | 131(8R) | >30 |
| 12 | 3 | 95(3R) | 101(4R) | 103(5R) | |
| 24 | 3 | 73(5R) | | | |
| 26 | 3 | 95(3R) | 102(4R) | 107(5R) | >30 |
| 37 | 4 | 47(3R) | 72(4R) | 88(5R) | >30 |
| α-hydroxypropiophenone (comparison) | 3 | 68(3R) | 75(4R) | 87(5R) | 1 |
| α-methylbenzoin (comparison) | 5 | 49(3R) | 69(4R) | 91(5R) | |
| benzoin-tert-butylether (comparison) | 5 | 93(5R) | 106(7R) | 113(9R) | <30 |
| 2-phenyl-dimethoxyacetophenone (comparison) | 6 | 112(6R) | 121(8R) | 130(10R) | >30 |
| p-methyl- | 8 | 92(8R) | 100(10R) | 109(12R) | <5 |
| α,α-dimorpholinoacetophenone (comparison) | | | | | |
| α,α-dimorpholinoacetophenone (comparison) | 17 | 84(17R) | 98(19R) | | <1 |

EXAMPLE 2

Resin mixtures consisting of 60 parts of Uvimer DV-530 (urethane acrylate, available from Polychrome), 37 parts of hexanedioldiacrylate and 3 parts of photosensitizer were applied in a film thickness of 30 μm to glass plates and irradiated as described in Example 1. The following results were obtained.

TABLE 3

| Photosensitizer | No. of runs necessary until wipe-proof | Pendulum hardness according to König as a function of R |
|---|---|---|
| 1 | 3 | 129(3R)<br>157(7R) |
| 2 | 3 | 144(3R)<br>163(7R) |
| diethoxyacetophenone (comparison) | 10 | 156(10R) |
| benzoin tert-butyl ether (comparison) | 12 | 136(12R) |
| 2-phenyldimethoxyacetophenone (comparison) | 8 | 155(8R) |

EXAMPLE 3

2% of photosensitizer was dissolved in an unsaturated polyester resin (Crystic PKE 306, available from Maeder, Killwangen, Switzerland). These resin mixtures were applied in a film thickness of 60 μm to glass plates. The films were irradiated as described in Example 1. The number of runs through the exposure device until the films were wipe-proof as well as the pendulum hardness as a function of R are reported in Table 4.

TABLE 4

| Photo-sensitizer | No. of runs necessary until wipe-proof | Pendulum hardness according to Konig as a function of R | | |
|---|---|---|---|---|
| 1 | 13 | 21(13R) | 34(15R) | 62(17R) |
| 2 | 8 | 20(8R) | 31(10R) | 89(12R) |
| 3 | 10 | 28(10R) | 71(12R) | 109(12R) |

EXAMPLE 4

A resin mixture consisting of 90 parts of Laromer LR 8496 (acrylate resin available from BASF, West Germany), 10 parts of hexanediol diacrylate, 0.5 part of ByK 300 (levelling assistant available from ByK-Mallinckrodt, West Germany) and 3 parts of photosensitizer for hardening in the air or 0.5 part of photosensitizer for hardening under nitrogen, is applied electromotively to cardboard boxes with a 15μ helix. After brief exposure to air, hardening is effected with a UV device (model PPG-QC-processer) with a UV lamp of 80 watts/cm. The maximum transportation speed at which non-tacky films were obtained in air or under nitrogen is reported in Table 5 in m/min.

TABLE 5

| Photosensitizer | Transportation speed (m/min) | |
|---|---|---|
| | air | nitrogen |
| 3 | 20 | 100 |
| 5 | 20 | 100 |
| 7 | 30 | 100 |
| 8 | 30 | 100 |
| 9 | 5 | 80 |
| 10 | 5 | 80 |
| 12 | 3.3 | 80 |
| 13 | 20 | 120 |
| 29 | 10 | 90 |
| 30 | 20 | 90 |

EXAMPLE 5

A resin mixture consisting of 70 parts of Ebercyl 593 (polyester acrylate available from UCB, Belgium), 30 parts of trimethylolpropane trisacrylate, 0.5 part of ByK 300 (levelling assistant available from ByK-Malinckrodt, West Germany) and 3 parts of photosensitizer, is applied to glass plates in a layer of 30–40μ. After brief exposure to air, hardening is effected with a UV laboratory device (model PPG/QC-processer) with a UV lamp of 80 watts/cm. After the UV hardening, the plates are stored for ½ hour under normal climatic conditions and then the hardness of the layers is determined using the pendulum device of König. The hardness values as a function of the transportation speed under the lamp are reported in Table 6.

TABLE 6

| Photosensitizer | Pendulum hardness in sec. | |
|---|---|---|
| | 10 m/min. | 25 m/min. |
| 3 | 154 | 146 |

TABLE 6-continued

| Photosensitizer | Pendulum hardness in sec. | |
|---|---|---|
| | 10 m/min. | 25 m/min. |
| 13 | 156 | 147 |
| 14 | 138 | 137 |
| 15 | 150 | 132 |
| 16 | 161 | 152 |
| 17 | 160 | 144 |
| 21 | 155 | 143 |
| 22 | 151 | 127 |
| 27 | 162 | 154 |
| 30 | 129 | 98 |
| 32 | 146 | 129 |
| 35 | 134 | 108 |
| 38 | 139 | 116 |
| 39 | 162 | 149 |
| 40 | 153 | 131 |
| 41 | 164 | 152 |

What is claimed is:

1. In a method for the photopolymerisation of unsaturated compounds or for the photochemical crosslinking of polyolefins employing a sensitizer, the improvement according to which the sensitizer is a compound of the formula

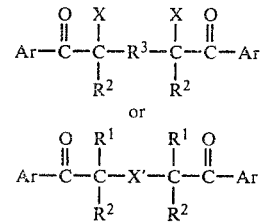

wherein

Ar is a member selected from the group consisting of phenyl, naphthyl, phenanthryl, anthracyl, diphenylyl, chlorophenyl, bromophenyl, dichlorophenyl, mesityl, isopropylphenyl, phenoxyphenyl, cyanophenyl, p-nonylphenyl, hydroxyphenyl, tolyl, tert-butylphenyl, xylyl, isopropylchlorophenyl, methoxyphenyl, ethoxyphenyl, phenoxyphenyl, chlorotolyl, bromoxylyl, methylthiophenyl, phenylthiophenyl, butylsulfophenyl, phenylsulfophenyl, ethoxycarbonylphenyl, tert-butoxycarbonylphenyl, methylaminosulfophenyl, dipropylaminosulfophenyl, dimethylaminophenyl, benzoylaminophenyl and acetylaminophenyl, X represents —OR⁶, X' represents

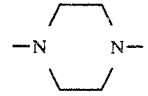

R¹ represents (a) $C_1-C_8$ alkyl, (b) $C_1-C_8$ alkyl substituted by —OH, Oalk, $C_2-C_8$ acyloxy, —NR⁴R⁵, —COOalk or —CN, (c) $C_3-C_4$ alkenyl, (d) $C_5-C_6$ cycloalkyl or (e) $C_7-C_9$ phenylalkyl, R² has one of the meanings assigned to R¹ or represents a —CH₂CH₂R¹³ group, or together with R¹ represents $C_2-C_8$ alkylene or $C_3-C_9$ oxaalkylene or $C_3-C_9$ azaalkylene, R³ represents a direct bond, $C_1-C_6$ alkylene, $C_2-C_6$ oxaalkylene, $C_2-C_6$ thiaalkylene, S-oxathiaalkylene or S-dioxathiaalkylene, phenylene, diphenylene or a -phenylene-T-phenylene group, or together with both substituents $R^2$ and both carbon atoms to which these substituents are attached, forms a cyclopentane, cyclohexene, endomethylenecyclohexane or cyclohexane ring, T represents —O—, —S—, —SO$_2$—, —CH$_2$—, —CH$_2$—CH$_2$—, —CH$_2$OCH$_2$— or —CH=CH—, $R^4$ represents (a) $C_1$-$C_{12}$ alkyl, (b) $C_2$-$C_4$ alkyl substituted by —OH, Oalk or —CN, (c) $C_3$-$C_5$ alkenyl, (d) cyclohexyl, (e) $C_7$-$C_9$ phenylalkyl, (f) phenyl or (g) phenyl which is substituted by Cl, alk, OH, Oalk or —COOalk, $R^5$ represents (a) $C_1$-$C_{12}$ alkyl, (b) $C_2$-$C_4$ alkyl which is substituted by —OH, Oalk or —CN, (c) $C_3$-$C_5$ alkenyl, (d) cyclohexyl or (e) $C_7$-$C_9$ phenylalkyl, or $R^4$ and $R^5$ together represent $C_4$-$C_5$ alkylene which can be interrupted by —O— or $$-\overset{|}{N}R^{14},$$

$R^6$ represents (a) hydrogen, (b) $C_1$-$C_{12}$ alkyl, (c) $C_1$-$C_8$ alkyl which is substituted by Cl, Br, OH, Oalk, Salk, $C_2$-$C_8$ acyloxy, —COOalk, CONHalk, —CON(alk)$_2$ or CN, (d) $C_3$-$C_5$ alkenyl, (e) cyclohexyl, (f) benzyl, (g) phenyl, (h) phenyl substituted by Cl or alk, or (i) 2-tetrahydropyranyl, $R^{13}$ represents —CONH$_2$, —CONHalk, —CON(alk)$_2$, —P(O)(Oalk)$_2$, 2-pyridyl or 2-oxo-1-pyrrolidinyl, and $R^{14}$ represents $C_1$-$C_4$ alkyl, —CH$_2$CH$_2$CN or —CH$_2$CH$_2$COOalk.

2. A method according to claim 1 wherein the sensitizer is a compound according to claim 1 wherein $R^1$ represents (a) alkyl of 1 to 8 carbon atoms, (b) alkyl of 1 to 8 carbon atoms substituted by OH, $C_1$-$C_4$ alkoxy, $C_2$-$C_8$ acyloxy, —COO—($C_1$-$C_4$)alkyl or —CN, (c) cycloalkyl of 5 or 6 carbon atoms, or (d) phenylalkyl of 7 to 9 carbon atoms, $R^2$ has one of the meanings assigned to $R^1$ or $R^1$ and $R^2$ together represent alkylene of 4 to 6 carbon atoms, oxaalkylene of 3 to 4 carbon atoms or azaalkylene of 3 to 4 carbon atoms, $R^3$ represents a direct bond, alkylene of 1 to 6 carbon atoms, oxaalkylene of 2 to 6 carbon atoms, phenylene, diphenylene, a phenylene-T-phenylene group, or both substituents $R^2$ together with $R^3$ and both carbon atoms to which these substituents are attached form a cyclopentane or cyclohexane ring, T represents —O—, —S—, —SO$_2$—, —CH$_2$— or —CH=CH—, $R^4$ represents (a) alkyl of 1 to 12 carbon atoms, (b) alkyl of 2 to 4 carbon atoms which is substituted by —OH or —Oalk, (c) allyl, (d) cyclohexyl, (e) phenylalkyl of 7 to 9 carbon atoms, (f) phenyl or (g) phenyl which is substituted by Cl, alk, OH, —Oalk or —COOalk, $R^5$ represents (a) alkyl of 1 to 12 carbon atoms, (b) alkyl of 2 to 4 carbon atoms which is substituted by —OH or —Oalk, (c) allyl, (d) cyclohexyl or (e) phenylalkyl of 7 to 9 carbon atoms, or $R^4$ and $R^5$ together represent alkylene of 4 to 5 carbon atoms which can be interrupted by —O—, —NH— or —Nalk—, and $R^6$ represents (a) hydrogen, (b) alkyl of 1 to 12 carbon atoms, (c) alkyl of 2 to 4 carbon atoms which is substituted by —OH or —Oalk, (d) allyl, (e) cyclohexyl, (f) benzyl, (g) phenyl, or (h) phenyl which is substituted by Cl or alk.

3. A method according to claim 1 wherein the sensitizer is a compound according to claim 1 wherein $R^1$ represents (a) alkyl of 1 to 8 carbon atoms, (b) alkyl of 1 to 8 carbon atoms substituted by OH, $C_1$-$C_4$ alkoxy, $C_2$-$C_8$ acyloxy, —COO—($C_1$-$C_4$)alkyl or —CN, (c) cycloalkyl of 5 to 6 carbon atoms, or (d) phenylalkyl of 7 to 9 carbon atoms, $R^2$ has one of the meanings assigned to $R^1$ or represents allyl, methallyl, 2-carbamoylethyl, 2-(N—C$_1$-$C_4$ alkylcarbamoyl)ethyl, 2-(N,N-di-$C_1$-$C_4$alkylcarbamoyl)ethyl, 2-(2-pyridyl)ethyl, 2-(2-oxo-1-pyrrolidinyl)ethyl or 2-(di-O-$C_1$-$C_4$alkylphosphono)ethyl, or $R^1$ and $R^2$ together represent alkylene of 4 to 6 carbon atoms, oxaalkylene of 3 to 4 carbon atoms, or azaalkylene of 3 to 4 carbon atoms, $R^3$ is a direct bond, alkylene of 1 to 6 carbon atoms, oxaalkylene of 2 to 6 carbon atoms, thialkylene of 2 to 6 carbon atoms, S-oxothiaalkylene of 2 to 6 carbon atoms, S,S-dioxathia-alkylene of 2 to 6 carbon atoms, phenylene, diphenylene or a -phenylene-T-phenylene group or cyclohexylene, or both substituents $R^2$ together with $R^3$ and both carbon atoms to which these substituents are attached form a cyclopentane or cyclohexane ring, T represents —O—, —S—, —SO$_2$—, —CH$_2$— or —CH=CH—, $R^4$ represents (a) alkyl of 1 to 12 carbon atoms, (b) alkyl of 2 to 4 carbon atoms which is substituted by —OH or —Oalk, (c) allyl, (d) cyclohexyl, (e) phenylalkyl of 7 to 9 carbon atoms, (f) phenyl or (g) phenyl which is substituted by Cl, alk, OH, —Oalk or —COOalk, $R^5$ represents (a) alkyl of 1 to 12 carbon atoms, (b) alkyl of 2 to 4 carbon atoms which is substituted by —OH or —Oalk, (c) allyl, (d) cyclohexyl or (e) phenylalkyl of 7 to 9 carbon atoms, or $R^4$ and $R^5$ together represent alkylene of 4 to 5 carbon atoms which can be interrupted by —O—, —NH— or —Nalk—, and $R^6$ represents (a) hydrogen, (b) alkyl of 1 to 12 carbon atoms, (c) alkyl of 2 to 4 carbon atoms which is substituted by —OH or —Oalk, (d) allyl, (e) cyclohexyl, (f) phenylalkyl of 7 to 9 carbon atoms, (g) phenyl or (h) phenyl which is substituted by Cl or alk.

4. A method according to claim 1 wherein the sensitizer is a compound according to claim 1 wherein $R^1$ represents (a) $C_1$-$C_8$ alkyl, (b) $C_1$-$C_8$ alkyl substituted by —OH, —Oalk, —COOalk or —CN, or (c) $C_7$-$C_9$ phenylalkyl, $R^2$ has one of the meanings assigned to $R^1$ or is alkyl or a —CH$_2$CH$_2$R$^{13}$ group, or together with $R^1$ represents $C_4$-$C_6$ alkylene or $C_3$-$C_4$ oxaalkylene or $C_3$-$C_4$ azaalkylene, $R^3$ represents a direct bond or $C_1$-$C_6$ alkylene or together with both substituents $R^2$ and both carbon atoms to which these substituents are attached forms a cyclopentane or cyclohexane ring, $R^4$ represents (a) $C_1$-$C_{12}$ alkyl, (b) $C_2$-$C_4$ alkyl which is substituted by OH or Oalk or (c) allyl, $R^5$ represents (a) $C_1$-$C_{12}$ alkyl, (b) $C_2$-$C_4$ alkyl which is substituted by OH or Oalk or (c) allyl or $R^4$ and $R^5$ together represent $C_4$-$C_5$ alkylene which can be interrupted by —O— or —Nalk—, $R^6$ represents (a) hydrogen, (b) $C_1$-$C_{12}$ alkyl, (c) $C_2$-$C_6$ alkyl which is substituted by OH or Oalk, (d) allyl, (e) benzyl or (f) phenyl, and $R^{13}$ represents —$CONH_2$, —CONHalk, —CON(alk)$_2$, —P(O)(Oalk)$_2$ or 2-pyridyl.

5. A method according to claim 1 wherein the sensitizer is a compound according to claim 1 wherein $R^1$ represents $C_1$-$C_8$ alkyl, $R^2$ represents $C_1$-$C_8$ alkyl or allyl, $R^3$ represents a direct bond or $C_1$-$C_6$ alkylene, $R^4$ represents $C_1$-$C_{12}$ alkyl, $R^5$ represents $C_1$-$C_{12}$ alkyl or together with $R^4$ represents $C_4$-$C_5$ alkylene which can be interrupted by —O— or —Nalk—, and $R^6$ represents (a) hydrogen, (b) $C_1$-$C_{12}$ alkyl, (c) $C_2$-$C_4$ alkyl which is substituted by OH or Oalk, (d) allyl, (e) benzyl, or (f) phenyl.

6. A method according to claim 1 wherein the sensitizer is a compound according to claim 1 wherein X represents alkoxy, $C_1$-$C_6$ hydroxyalkoxy, alkoxyalkoxy, benzyloxy or phenyloxy.

7. A method according to claim 1 wherein the sensitizer is a compound according to claim 1 wherein Ar represents p-phenoxy-phenyl.

8. A photopolymerisable system comprising at least one unsaturated photopolymerisable compound and 0.1 to 20% by weight of a compound according to claim 1 as photosensitizer.

9. A photopolymerisable system according to claim 8 wherein the amount of the compound is 0.5 to 5% by weight.

10. A photopolymerisable system according to claim 8 which contains one or more esters of acrylic or methacrylic acid as unsaturated compound.

11. A photopolymerisable system according to claim 8 which is a printing ink.

12. A photochemically crosslinkable system comprising a polyolefin and 0.1 to 20% by weight of a compound according to claim 1 as photosensitizer.

13. A system according to claim 12 wherein the amount of the compound is 0.5 to 5% by weight.

14. A photochemically crosslinkable system according to claim 12 wherein the polyolefin is a polyethylene.

* * * * *